United States Patent [19]
Morioka et al.

[11] Patent Number: 4,584,134
[45] Date of Patent: Apr. 22, 1986

[54] PROCESS FOR THE RECOVERY OF NOSIHEPTIDE

[75] Inventors: Satoshi Morioka; Makoto Shida; Nobuyuki Suzuki; Kiyoshi Sekihara, all of Yokohama, Japan

[73] Assignee: Rhone-Poulenc Sante, Courbevoie, France

[21] Appl. No.: 626,194

[22] Filed: Jun. 29, 1984

[30] Foreign Application Priority Data

Jul. 4, 1983 [JP] Japan .................................. 58-121273

[51] Int. Cl.$^4$ ............................................. C07D 515/22
[52] U.S. Cl. ............................................... 260/239.3 P
[58] Field of Search .................................. 260/239.3 P

[56] References Cited

U.S. PATENT DOCUMENTS 4,175,126 11/1979 Lombardi et al. ........... 260/239.3 P

Primary Examiner—Robert T. Bond
Attorney, Agent, or Firm—Stevens, Davis, Miller & Mosher

[57] ABSTRACT

Nosiheptide, a valuable antibiotic used as an animal feed additive, is separated from a culture containing the same by extraction with a cyclic ether, preferably tetrahydrofuran.

4 Claims, No Drawings

PROCESS FOR THE RECOVERY OF NOSIHEPTIDE

The present invention relates to recovery of the antibiotic Nosiheptide from a culture containing the same.

Nosiheptide (also called 9671RP) is an antibiotic produced by a strain of the genus Streptomyces (see Japanese patent publication No. 880/1965) and is used as a feed additive for animals.

To prepare Nosiheptide, the Nosiheptide-producing strain of the genus Streptomyces is cultured and Nosiheptide is recovered from the culture by mixing it with a solvent, and separating the mycelia insoluble in the solvent. The selection of the proper solvent is very important. The solvent is required to have good separability from a solvent-insoluble portion having mycelium as a main component and a good solvent power for the antibiotic.

The solvent varies according to the mycelium or antibiotic which is to be separated. For example, a method using acetone, methanol and ethanol is known (see Japanese patent publication No. 29157/73) for separating and recovering multhiomycin from the culture obtained by cultivating a multhiomycin-producing strain belonging to the genus Streptomyces. Further, a method using chloroform or a mixed solvent containing chloroform as a main component is known (see Japanese patent publication No. 26718/70) for separating and recovering thiopeptin B from the culture obtained by cultivating a thiopeptin B-producing strain belonging to the genus Streptomyces. However, the solvent power of such known solvents for Nosiheptide is too small to be adequate.

In this situation, it is an object of the present invention to provide an effective method for the separation and recovery of Nosiheptide. This object is achieved by using a cyclic ether as a solvent in a process for the separation and recovery of Nosiheptide from a culture of a Nosiheptide-producing strain of the genus Streptomyces by mixing the said culture with a solvent, separating a solvent-insoluble portion having mycelium as a main component, and recovering Nosiheptide from the solvent.

As the Nosiheptide-producing strain, *Streptomyces actuosus* (NRRL 2954: ATCC 25421) or a mutant thereof may be used. The aforesaid strains are publicly available from Agriculture Research Culture Collection (NRRL), U.S. Department of Agriculture, Science and Educational Administration, Northern Regional Research Center, Peoria, Ill., and American Type Culture Collection (ATCC) 12301 Parklawn Drive, Rockville, Md. 20852, under the aforesaid deposit numbers.

The culture containing Nosiheptide may be obtained by cultivating such a strain according to the method described in Japanese patent publication No. 880/1965. The cultivation medium contains carbohydrates, inorganic salts, and other conventional nutrients suitable for the strain used. Nosiheptide is accumulated on the surface of the mycelium produced by the actinomycete and having a complicated surface structure.

In the method of the present invention the culture (broth) is mixed in a cyclic ether.

Suitable cyclic ethers include tetrahydrofuran, dioxane and the like. Tetrahydrofuran is preferred.

The culture treated with the cyclic ether may be either broth which has been subjected to a dehydration treatment by a mechanical device, such as a centrifugal separator or filter, or crude broth which has not been subjected to a dehydration treatment.

It is difficult to carry out mechanical dehydration on a broth containing mycelium of complicated surface structure. However, the cyclic ether used in this invention has an excellent solvent effect on Nosiheptide even if crude broth of high moisture content is used. Thus, it is economically advantageous to use crude broth when carrying out the treatment with the cyclic ether.

The amount of cyclic ether used depends on the content of water and Nosiheptide in the culture, but is generally fom 0.5 to 5 times by volume, preferably 1.5 to 2.5 times by volume, that of the culture.

The treatment with the cyclic ether is generally performed in a stirring tank with an outlet for insoluble matter at the bottom. The treatment time is usually 0.5 to 3 hours, preferably 1 to 2 hours, and the temperature is usually 5° to 80° C., preferably room temperature to 60° C.

The pH of the culture subjected to the treatment varies according to the cultivation condition. It is preferable to adjust pH to within the range of 3 to 10, more preferably 5 to 7, for the treatment. This adjustment prevents the Nosiheptide from transferring in to the water layer and makes recovery higher, especially when a water layer is separated to remove impurities as described below.

After the treatment with the cyclic ether, the mixture of culture and solvent is left to stand to form two phases, a solid insoluble phase having mycelium as a main component, and a clear solvent phase containing dissolved Nosiheptide (this clear solvent contains much water, and is hereinafter referred to as 37 the cyclic ether extract"). The phases are separated by discharging the precipitated insoluble matter through the outlet on the bottom of the stirring tank.

One such extraction treatment is usually enough since the cyclic ether has high solvent power for Nosiheptide. However, the separated insoluble matter can be treated with cyclic ether again if necessary.

The Nosiheptide dissolved in the cyclic ether extract is then recovered therefrom. Before this recovery, it is preferable to add an inorganic salt or, preferably, a second solvent soluble in the cyclic ether, but only slightly soluble or insoluble in water, to the cyclic ether extract, in order to form an aqueous phase composed of water dissolved in the cyclic ether, and then to remove the aqueous phase.

The material used as salting out agent may be an inorganic salt such as magnesium chloride, sodium chloride, or calcium chloride. Benzene, toluene, xylene, hexane, heptane or cyclohexane may be used as a solvent insoluble in water. The amount used varies according to the amount of water in the cyclic ether extract. For example, the amount of the solvent slightly soluble in water may be 0.05 to 0.5 times by volume, preferably 0.25 to 0.35 times by volume, that of the cyclic ether. When the amount of the solvent is smaller than this range, not all the water dissolved in the cyclic ether can be separated. On the other hand, when larger amounts of solvent are used, the Nosiheptide is precipitated from the cyclic ether.

The formation of the aqueous phase can be carried out using the same stirring tank as that used to extract the culture, so that, following separation of insoluble matter, the inorganic salt or the second solvent insoluble in water is added and mixed with the cyclic ether in the tank at the same temperature as that of the treatment with the cyclic ether for 1 to 10 minutes.

When the aqueous phase is separated, impurities such as carbohydrates and inorganic salts dissolved in the cyclic ether extract are separated together with the water, and highly purified Nosiheptide is recovered directly from the cyclic ether. A little Nosiheptide may be lost by transfer to the aqueous phase. This loss can, however, be effectively prevented by adjusting the pH of the culture subjected to the treatment with the cyclic ether to within the range described herein.

The Nosiheptide may be recovered from the cyclic ether extract either by precipitating Nosiheptide by distillation of solvent and then recovering it mechanically, or by precipitating Nosiheptide by adding a third component to the cyclic ether extract after separation of the aqueous phase. It is preferable to use as the third component the same solvent as that used for the separation of the aqueous phase.

The amount of such solvent (the third component) used for separating the Nosiheptide may be 0.2 to 1.0 times by volume, preferably 0.4 to 0.6 times by volume, that of the cyclic ether after separation of the aqueous phase. However, if water is not separated, the amount may be 0.25 to 1.5 times by volume, preferably 0.65 to 0.95 times by volume, that of the cyclic ether.

The treatment is carried out under the same condition as the separation of the aqueous phase. That is, the solvent is added to the stirring tank after separation of the aqueous phase.

The recovery of the Nosiheptide precipitated from the cyclic ether can be easily performed by centrifugal separation or filtration.

The Nosiheptide thus recovered sometimes contains a small amount of heavy metals such as Fe, Co, Ni, Cu and Mn. If it is necessary to remove such heavy metals, the Nosiheptide should be dissolved in an appropriate solvent and treated with activated charcoal, silica gel, or chelate ion-exchange resin.

The separation of heavy metals can also be carried out on the cyclic ether extract after separation of the aqueous phase as described above.

The present invention makes it possible to carry out the separation and recovery of Nosiheptide from a culture effectively and economically.

The present invention is illustrated by the following example.

EXAMPLE

A mixing tank with an outlet on the bottom is charged with 100 parts by volume of culture (broth), obtained by cultivating *Streptomyces actuosus,* and with 200 parts by volume of tetrahydrofuran and mixed with stirring at a temperature of 60° C. for 1 hour.

The composition of the culture was as follows (in percentages by weight):

| | |
|---|---|
| mycelium: | 7.5 |
| carbohydrates: | 2.0 |
| inorganic salts: | 0.5 |
| nosiheptide: | 0.5 |
| water: | 89.5 |
| The pH was | 5.6 |

The mixture is allowed to stand for 5 minutes to precipitate insoluble matter, and then the insoluble matter is discharged through the outlet. The amount of insoluble matter is 75 parts by volume and that of the tetrahydrofuran solution in the tank is 255 parts by volume. Analysis by liquid chromatography shows that the solvent contains 2.11 wt% of Nosiheptide (recovery 95 wt%).

60 parts by volume of heptane are then added to the tank and mixed for 5 minutes. The mixture is allowed to stand for 10 minutes and the lower, aqueous phase formed is discharged through the outlet. The amount of discharged water is 60 parts by volume, and 225 parts by volume of the cyclic ether extract remains. 95 wt% and 99 wt% respectively of carbohydrates and inorganic salts are rmoved in the aqueous phase. These removal rates are determined in the following way:

carbohydrates: After addition of water, the cyclic ether extract is filtered to separate the precipitated Nosiheptide, and the residue obtained by distilling and drying the filtrate is dissolved in water. Then, after adding colour-forming reagents, optical absorbance is measured.

inorganic salts: atomic absorption analysis is carried out on the cyclic ether extract.

100 parts by volume of heptane are then again added to the tetrahydrofuran after removal of the aqueous phase and the mixture is stirred for 5 minutes. The whole contents are discharged from the tank and conveyed to a centrifugal separator. The Nosiheptide is then recovered. The concentration of Nosiheptide in the separated solvent is only a trace, and the purity of the Nosiheptide recovered is 95 wt% according to liquid chromatography analysis.

Reference Example

The solubility of Nosiheptide in the culture used in Example 1 in several solvents is shown in Table 1 below.

The rating of solubility is in accordance with "Ministerial ordinance concerning the specification on the component of feed and feed additive".

TABLE 1

| Solvent | Solubility |
|---|---|
| ethanol | Very slightly soluble |
| Isopropanol | Slightly soluble |
| amyl alcohol | Slightly soluble |
| toluene | Slightly soluble |
| chloroform | Slightly soluble |
| dichloromethane | Very slightly soluble |
| dichloroethane | Very slightly soluble |
| ethyl acetate | Very slightly soluble |
| isobutyl acetate | Very slightly soluble |
| acetone | Slightly soluble |
| methyl isobutyl ketone | Slightly soluble |
| tetrahydrofuran | Soluble |

We claim:

1. In a process for the separation and recovery of Nosiheptide from a culture of a Nosiheptide-producing strain of the genus Streptomyces by mixing the said culture with a solvent, separating a solvent-insoluble portion having mycelium as a main component, and recovering Nosiheptide from the solvent, the improvement which consists in using a cyclic ether as the said solvent.

2. A process according to claim 1, wherein the said cyclic ether is tetrahydrofuran.

3. A process according to claim 1, wherein the amount of the said solvent used is from 0.5 to 5 times by volume that of the culture.

4. A process according to claim 1, wherein a second solvent which is miscible with the cyclic ether but only slightly soluble in water is added, in an amount of from 0.05 to 0.5 times by volume that of the cyclic ether, to the mixture of the culture and the cyclic ether to form an aqueous phase composed of water dissolved in the cyclic ether and the water is separated from the cyclic ether before the Nosiheptide is recovered from the cyclic ether.

* * * * *